US006306375B1

(12) United States Patent
Ellingson et al.

(10) Patent No.: US 6,306,375 B1
(45) Date of Patent: *Oct. 23, 2001

(54) LONG WEAR NAIL POLISH HAVING DEFINED SURFACE PROPERTIES

(75) Inventors: Peter Christopher Ellingson, Hamilton; Edward Dewey Smith, III, Mason, both of OH (US)

(73) Assignee: The Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/071,423

(22) Filed: May 1, 1998

(51) Int. Cl.[7] .............................. A61K 6/00; A61K 7/00; A61K 7/04
(52) U.S. Cl. ............................................. 424/61; 424/401
(58) Field of Search ..................... 424/401, 61; 427/389; 132/73

(56) References Cited

U.S. PATENT DOCUMENTS

| 4,277,380 | 7/1981 | Williams et al. ............... 260/18 |
| 4,384,058 | 5/1983 | Galante ............................ 524/32 |
| 4,431,763 | 2/1984 | Reed ................................ 524/389 |
| 4,442,259 | 4/1984 | Isgur et al. ..................... 524/839 |
| 4,766,005 | 8/1988 | Montgomery et al. ........... 427/4 |
| 4,812,492 | 3/1989 | Eckes et al. ..................... 523/351 |
| 4,844,102 | 7/1989 | Repensek et al. ............... 132/17 |
| 5,120,529 | 6/1992 | Koch et al. ..................... 424/61 |
| 5,266,322 | 11/1993 | Myers et al. ................... 424/401 |
| 5,284,885 | 2/1994 | Wehra ............................ 524/31 |
| 5,380,520 | 1/1995 | Dobbs ............................ 424/61 |
| 5,538,717 | 7/1996 | La Poterie ..................... 424/61 |
| 5,607,665 | 3/1997 | Calello et al. ................. 424/61 |
| 5,681,550 | * 10/1997 | Rubino ........................ 424/61 |
| 5,716,603 | 2/1998 | Chen et al. ................... 424/61 |
| 5,811,084 | 9/1998 | Busch, Jr. et al. ............. 424/61 |
| 5,882,635 | 3/1999 | Ramin et al. ................. 424/61 |

FOREIGN PATENT DOCUMENTS

| 87242557 | 8/1987 | (CA) . |
| 0 061348 A1 | of 0000 | (EP) . |
| 0 022452 A1 | 1/1981 | (EP) . |
| 0 063467 A1 | 10/1982 | (EP) . |
| 0 325038 A2 | 7/1989 | (EP) . |
| 0 418469 A1 | 3/1991 | (EP) . |
| 0 455373 A1 | 6/1991 | (EP) . |
| 0 680742 A1 | 6/1991 | (EP) . |
| 0 627212 | 5/1993 | (EP) . |
| 0 619 111 A1 | 12/1994 | (EP) . |
| 0299758 B1 | 12/1994 | (EP) . |
| 0 636361 | 2/1995 | (EP) . |
| 0 637600 A1 | 2/1995 | (EP) . |
| 0 679384 | 11/1995 | (EP) . |
| 0 705594 A1 | 4/1996 | (EP) . |
| 0 658609 A1 | 10/1997 | (EP) . |
| 0 797977 A1 | 10/1997 | (EP) . |
| 57-23632 | 2/1982 | (JP) . |
| 4-103512 | 4/1992 | (JP) . |
| 4-103513 | 4/1992 | (JP) . |
| 4-103514 | 4/1992 | (JP) . |
| 5-148122 | 6/1993 | (JP) . |
| 5-155737 | 6/1993 | (JP) . |
| 5-310531 | 11/1993 | (JP) . |
| 7-309721 | 11/1995 | (JP) . |
| 9-157135 | 6/1997 | (JP) . |
| 9-268113 | 10/1997 | (JP) . |
| 883078 | 11/1981 | (SU) . |
| WO 92/16185 | 3/1992 | (WO) . |
| WO 92/05762 | 4/1992 | (WO) . |
| WO 96/34061 | 10/1996 | (WO) . |
| WO 97/00664 | 1/1997 | (WO) . |
| WO 9742930 | 11/1997 | (WO) . |

OTHER PUBLICATIONS

U.S. application No. 09/070,960, Ellingson et al., filed May 1, 1998.

U.S. application No. 09/071,424, Ellingson et al., filed May 1, 1998.

U.S. application No. 09/071,098, Ellingson et al., filed May 1, 1998.

U.S. application No. 09/071,097, Smith et al., filed May 1, 1998.

U.S. application No. 09/071,273, Ellingson et al., filed May 1, 1998.

U.S. application No. 09/071,099, Ellingson et al., filed May 1, 1998.

U.S. application No. 60/083,020, Pichardo et al., filed Aprl. 24, 1998.

* cited by examiner

Primary Examiner—Thurman K. Page
Assistant Examiner—Sharon Howard
(74) Attorney, Agent, or Firm—Darryl C. Little; Loretta J. Henderson

(57) ABSTRACT

The present invention relates to compositions, kits, and films formed therefrom which are useful as cosmetic or therapeutic agents, as well as methods of their use. The compositions, kits, and films herein are particularly useful as polishes for mammalian nails. More particularly, the present invention relates to compositions and kits which, when applied to mammalian nails form films exhibiting long wear. When applied to mammalian nails, the present kits and compositions form films exhibiting surface energies from about 32 mN/m to about 43 mN/m and polarities from about 0.19 to about 0.29. The present invention further relates to methods of coating mammalian nails with films exhibiting surface energies from about 32 mN/m to about 43 mN/m and polarities from about 0.19 to about 0.29.

23 Claims, No Drawings

LONG WEAR NAIL POLISH HAVING DEFINED SURFACE PROPERTIES

TECHNICAL FIELD

The present invention relates to compositions and kits useful as cosmetic or therapeutic agents and films formed therefrom having defined surface energy and polarity properties. The compositions, kits, and films herein are particularly useful as polishes for mammalian nails.

BACKGROUND OF THE INVENTION

Consumers use nail polishes to cosmetically enhance their nails or protect the nails from everyday conditions and stressors. However, these nail polish compositions are deficient in many respects, including their inability to provide long wear. Nail polishes which are known or currently available often exhibit deterioration, particularly in the form of chipping or peeling, in as few as one or two days. Such poor wear often forces consumers to remove their nail polish soon after original application and reapply additional nail polish to the nails. Consumers may also attempt to correct the unsightly appearance of the deteriorating nail polish by "touching-up" the areas of the nail which exhibit the deterioration, a practice which actually impairs the overall look of the nail polish. Finally, consumers may choose to do nothing about the deterioration and allow, for example, chipping and peeling to progress, resulting in nails which are not only minimally protected from the environment but are unsightly as well.

The art is replete with nail polish compositions which are promoted as having long wear, good adhesion, and/or resistance to chipping. While some nail polish compositions provide better wear than others, a need remains for nail polish compositions providing long wear.

Extreme examples of nail polish compositions which exhibit inadequate adhesion are those which are easily and completely peeled or stripped off the nails without the use of a solvent. See, e.g., EP 0,680,742, Mellul et al., assigned to L'Oreal.

Furthermore, other nail polish compositions are completely removable with water and, therefore, are not practical for normal use and do not provide adhesive and/or long wear properties under everyday conditions. See, e.g., JP 05-155,737, Itsumi et al., assigned to Yuho Chemical Co. Ltd. and EP 0,679,384, Ramin et al., assigned to L'Oreal.

It would therefore be desirable to provide nail polish compositions having improved wear properties including, for example, improved adhesion to the nail. It has been discovered that nail polishes exhibiting surface energies and polarities over defined ranges, as described herein, provide enhanced adhesion of nail polish to the nail. The present inventors have surprisingly discovered nail polish compositions and kits which, when applied to mammalian nails, form films which meet these ranges. Accordingly, by virtue of their adhesive properties, the present compositions and kits provide nail polish films exhibiting long wear at a superior level not provided by the nail polishes which are presently known and used.

SUMMARY OF THE INVENTION

The present invention relates to compositions and kits which provide films exhibiting defined surface properties, namely surface energies and/or polarities. The present kits comprise two or more compositions, preferably a basecoat composition, a topcoat composition, and, optionally, a midcoat composition, wherein at least one of the compositions, preferably the basecoat composition, provides defined surface properties as defined herein. Each composition comprises a film-forming polymer, a liquid diluent, and, optionally, other components. The present film-forming polymers are selected from polyurethanes, polyacryls, polymethacryls, cellulosic polymers, styrene-acryl copolymers, polystyrene-polyacryl mixtures, polysiloxanes, polyesters, urethane-acryl copolymers, siloxane-urethane copolymers, polyurethane-polymethacryl mixtures, silicone-acryl copolymers, vinyl acetate polymers, and mixtures thereof. When applied to mammalian nails, the basecoat compositions and kits comprising the basecoat compositions provide films exhibiting surface energies from about 32 mN/m to about 43 mN/m, more preferably from about 34 mN/m to about 42 mN/m, and/or polarities from about 0.19 to about 0.29, more preferably from about 0.20 to about 0.24. Compositions providing these properties comprise the film-forming polymer and a carrier comprising water and at least about 20% of a volatile organic solvent.

DETAILED DESCRIPTION OF THE INVENTION

The essential components of the present invention are herein described below. Also included are non-limiting descriptions of various optional and preferred components useful in the compositions and kits of the present invention.

The present invention can comprise, consist of, or consist essentially of any of the required or optional components and/or limitations described herein.

All percentages and ratios are calculated by weight unless otherwise indicated. All percentages are calculated based on the total composition unless otherwise indicated.

All component or composition levels are in reference to the active level of that component or composition, and are exclusive of impurities, for example, residual solvents or by-products, which may be present in commercially available sources.

Referred to herein are trade names for materials including, but not limited to, polymers and optional components. The inventors herein do not intend to be limited by materials under a certain trade name. Equivalent materials (e.g., those obtained from a different source under a different name or catalog (reference) number) to those referenced by trade name may be substituted and utilized in the kits, films, and methods herein.

All documents referred to herein, including all patents, patent applications, and printed publications, are hereby incorporated by reference in their entirety.

The compositions, kits, and films of the present invention are suitable for use as a nail polish for mammalian nails. As used herein, the term "suitable for use as a nail polish for mammalian nails" means that the compositions, kits, or films thereof are suitable for use in contact with mammalian nails without undue toxicity, incompatibility, instability, allergic response, and the like.

As used herein, the term "nail polish" is a comprehensive term describing a nail polish composition, film, product (including coloring products), system, kit, or the like, which is useful for providing, for example, aesthetic, therapeutic, or prophylactic benefits to the nail.

As used herein, the term "mammalian nail" means a keratinaceous plate present at the upper surface of the end of a finger or toe of a primate, most preferably a human, or the homologous claw or hoof of another mammal.

The layers and films herein may be joined to mammalian nails. As used herein, the terms "joined to", "joined to mammalian nails", or the like means in contact with or applied to a mammalian nail through physical forces in such a manner that the layer or film is contiguous to either the nail itself, a preceding layer, a succeeding layer, or matter previously applied to or existing on the nail. The layer or film may be "joined to" a mammalian nail, preceding layer, or succeeding layer even though other matter (such as another preceding or succeeding layer) intervenes. Accordingly, matter which is "joined to", for example, a mammalian nail, need not actually be contiguous to that mammalian nail.

As used herein, the term "contiguous to" means directly joined to by physical forces through touching and boundary sharing with essentially no intervening matter.

As used herein, the term "film" means one or more layers of a nail polish suitable for use on mammalian nails which forms when one or more compositions of the kit is applied to, and dries on, mammalian nails.

As used herein, the term "layer" means one substantially dry coat of nail polish which forms when a composition is applied to, and dries on, a mammalian nail.

As used herein, the term "preceding layer" means a layer which is joined to a nail and is closer in proximity to the nail as compared to a reference layer joined to the same nail. For example, wherein a basecoat and a topcoat are joined to a nail, the basecoat is a preceding layer relative to the topcoat. Similarly, wherein a basecoat, midcoat, and topcoat are joined to a nail, the basecoat and midcoat are preceding layers relative to the topcoat, and the basecoat is a preceding layer relative to both the midcoat and topcoat.

As used herein, the term "succeeding layer" means a layer which is joined to a nail and is further in proximity from the nail as compared to a reference layer joined to the same nail. For example, wherein a basecoat and a topcoat are joined to a nail, the topcoat is a succeeding layer relative to the basecoat. Similarly, wherein a basecoat, midcoat, and topcoat are joined to a nail, the midcoat and topcoat are succeeding layers relative to the basecoat, and the topcoat is a succeeding layer relative to both the basecoat and midcoat.

As used herein, the term "substantially dry" in reference to a film or a layer means that the film or layer feels dry, smooth, or not tacky when it is touched with a human fingertip.

Compositions, Kits, and Films of the Present Invention

The compositions and kits of the present invention, when applied to mammalian nails, provide films exhibiting long wear and good adhesion as defined by their surface energy and/or polarity. The kits comprise two or more compositions, preferably a basecoat composition, a topcoat composition, and, optionally, a midcoat composition. Each composition comprises a film-forming polymer, a liquid diluent, and, optionally, one or more other suitable components as described herein. As used herein, the term "film-forming polymer" means a homopolymer, copolymer, or mixture thereof which forms an adherent continuum from a composition when applied to mammalian nails. See. e.g., *Polymer Colloids*, Robert M. Fitch, ed., New York: Plenum Press, pp. 173–183 (1971). As used herein, the term "copolymer" includes linear, block, branched, graft, comb, and star copolymers.

Although the term "film-forming polymer" is used herein to describe a polymer in a composition, in some circumstances, polymerization may not actually take place until application of the composition (to the nail, for example) is performed. Accordingly, as used herein, the term "film-forming polymer" is meant to encompass monomers which have not yet polymerized but will upon application to the nail.

The film-forming polymers herein are preferably self-curing polymers. That is, the preferred polymers do not require chemical reaction or introduction of energy (e.g., exposure to ultraviolet rays) to form the adherent continuum.

The film-forming polymers herein can be selected from nonionic, ionic (anionic or cationic), and amphoteric (including zwitterionic) polymers. Wherein the film-forming polymer is water-borne, the polymer is preferably anionic.

The film-forming polymers herein are preferably, but are not limited to, solvent-borne or water-borne polymers. As used herein, the term "water-borne", with reference to a film-forming polymer, means that the polymer was prepared in a mixture comprising water and is preferably added to the composition which it comprises as a mixture (preferably a dispersion) in water. As used herein, the term "solvent-borne", with reference to a film-forming polymer, means that the polymer was prepared under substantially anhydrous conditions and is preferably added to the composition which it comprises as a substantially anhydrous mixture (preferably a solution).

Preferred film-forming polymers of the present invention are selected from polyurethanes, polyacryls, polymethacryls, cellulosic polymers, styrene-acryl copolymers, polystyrene-polyacryl mixtures, polysiloxanes, polyesters, urethane-acryl copolymers, siloxane-urethane copolymers, polyurethane-polymetliacryl mixtures, silicone-acryl copolymers, vinyl acetate polymers, and mixtures thereof. The term "polyacryl" includes polyacrylates, polyacrylics, and polyacrylamides. The term "polymethacryl" includes polymethacrylates, polymethacrylics, and polymethacrylamides. The term "cellulosic polymers" includes all cellulose polymers, including esters thereof.

Examples of preferred polyacryls, polymethacryls, and styrene-acryl copolymers include Gelva® 2497 (commercially available from Monsanto Co., St. Louis, Mo.), Durapluse® 2 (commercially available from Rohm & Haas Co., Philadelphia, Pa.), Joncryl® 95 (commercially available from S. C. Johnson Polymer, Sturtevant, WI), SCX-1537 (S. C. Johnson Polymer), SCX-1959 (S. C. Johnson Polymer), SCX-1965 (S. C. Johnson Polymer), Joncryl® 530 (S. C. Johnson Polymer), Joncryl® 537 (S. C. Johnson Polymer), Glascol LS20 (commercially available from Allied Colloids, Suffolk, Va.), Glascol C37 (Allied Colloids), Glascol LS26 (Allied Colloids), Glascol LS24 (Allied Colloids), Glascol LE45 (Allied Colloids), Surcol 441® (Allied Colloids), Carboset® CR760 (commercially available from BFGoodrich, Cleveland, Ohio), Carboset® CR761 (BFGoodrich), Carboset® CR763 (BFGoodrich), Carboset® 765 (BFGoodrich), Carboset® 19X2 (BFGoodrich), Carboset® XL28 (BFGoodrich), Hycar 26084 (BFGoodrich), Hycar 26091 (BFGoodrich), Carbobond 26373 (BFGoodrich), Neocryl® A-601 (commercially available from Zeneca Resins, Wilmington, Mass.), Neocryl® A-612 (Zeneca Resins), Neocryl® A-6044 (Zeneca Resins), Neocryl® A-622 (Zeneca Resins), Neocryl® A-623 (Zeneca Resins), Neocryl® A-634 (Zeneca Resins), and Neocryl® A-640 (Zeneca Resins).

An example of a preferred polysiloxane is PSA 590 (commercially available from General Electric, Waterford, N.Y.).

Examples of preferred urethane-acryl copolymers include Sancure® AU-4000 (commercially available from BFGoodrich), Sancure® AU-4010 (BFGoodrich), Witcobond A-100 (commercially available from Witco Performance Chemicals, Houston, Tex.), Witcobond W-610 (Witco Performance Chemicals), NeoPac R-9000 (commercially available from Zeneca Resins), NeoPac R-9030 (Zeneca Resins), and NeoPac R-9699 (Zeneca Resins).

Preferred polyurethanes are selected from aromatic polyether polyurethanes, aliphatic polyether polyurethanes, aromatic polyester polytiretlhanes, aliphatic polyester polyurethanes, aromatic polycaprolactam polyurethanes, and aliphatic polycaprolactam polyurethanes. The more preferred polyurethanes are selected from aromatic polyether polyurethanes, aliphatic polyether polyurethanes, aromatic polyester polyurethanes, and aliphatic polyester polyurethanes. Examples of preferred polyurethanes include Sancure 2710® and/or Avalure UR 445® (which are equivalent copolymers of polypropylene glycol, isophorone diisocyanate, and 2,2-dimethylolpropionic acid, having the International Nomenclature Cosmetic Ingredient name "PPG-17/PPG-34/IPDI/DMPA Copolymer"), Sancure 878®, Sancure 815®, Sancure 1301®, Sancure 2715®, Sancure 1828®, Sancure 2026®, Sancure 1818®, Sancure 853®, Sancure 830®, Sancure 825®, Sancure 776®, Sancure 850®, Sancure 12140®, Sancure 12619®, Sancure 835®, Sancure 843®, Sancure 898®, Sancure 899®, Sancure 1511®, Sancure 1514®, Sancure 1517®, Sancure 1591®, Sancure 2255®, Sancure 2260®, Sancure 2310®, Sancure 2725®, and Sancure 12471® (all of which are commercially available from BFGoodrich, Cleveland, Ohio), Bayhydrol DLN (commercially available from Bayer Corp., McMurray, Pa.), Bayhydrol LS-2033 (Bayer Corp.), Bayhydrol 123 (Bayer Corp.), Bayhydrol PU402A (Bayer Corp.), Bayhydrol 110 (Bayer Corp.), Witcobond W-320 (commercially available from Witco Performance Chemicals), Witcobond W-242 (Witco Performance Chemicals), Witcobond W-160 (Witco Performance Chemicals), Witcobond W-612 (Witco Performance Chemicals), Witcobond W-506 (Witco Performance Chemicals), NeoRez R-940 (commercially available from Zeneca Resins), NeoRez R-960 (Zeneca Resins), NeoRez R-962 (Zeneca Resins), NeoRez R-966 (Zeneca Resins), NeoRez R-967 (Zeneca Resins), NeoRez R-972 (Zeneca Resins), NeoRez R-9409 (Zeneca Resins), NeoRez R-9637 (Zeneca), NeoRez R-9649 (Zeneca Resins), and NeoRez R-9679 (Zeneca Resins).

Preferred solvent-borne polyurethanes include Sanres EX499® (hexylene glycol/neopentyl glycol/isophorone diisocyanate copolymer, Sanres 12711®, Sanres 6010®, and Sanres 6012® (all of which are available from BFGoodrich). The most preferred solvent-borne polyurethane is Sanres EX499®.

Examples of preferred water-borne polyester polyuretlianes include Sancure® 2060and Sancure® 815 (both of which are commercially available from BFGoodrich).

The most preferred water-borne polyurethanes are aliphatic polyether polyurethanes. Examples of preferred aliphatic polyether polyurethianies include Sancure 2710® and/or Avalure UR 4451®, Sancure 878®, NeoRez R-966, NeoRez R-967, and Witcobond W-320.

Preferred cellulosic polymers include, for example, nitrocellulose, cellulose acetate butyrate, and cellulose acetate propionate. The most preferred cellulosic polymer is nitrocellulose. Exemplary nitrocellulose polymers are nitrocellulose RS types (nitrogen content of 11.5% to 12.2%), commercially available from Hercules, such as nitrocellulose RS ½ second, nitrocellulose RS ¼ second, nitrocellulose RS ⅛ second, and nitrocelluose RS ¹⁄₁₆ second, and the like. Wherein a composition comprises a cellulosic polymer, the composition preferably comprises a plasticizer.

The compositions of the present invention further comprise a carrier comprising a liquid diluent. The liquid diluent comprises water, organic solvent, or mixtures thereof. Preferred organic solvents include those which are volatile. Preferred volatile organic solvents, at atmospheric pressure, have a boiling point of from about 50° C. to about 140° C., more preferably from about 56° C. to about 125° C., and most preferably from about 56° C. to about 98° C. Wherein the film-forming polymer utilized is water-borne, the organic solvent is preferably water-miscible.

Preferred organic solvents are selected from alcohols, esters, ketones, aromatic hydrocarbons, aliphatic hydrocarbons, ethers, and mixtures thereof. Alcohols and esters are more preferred. Preferred alcohols are monohydric. The most preferred monohydric alcohols are ethanol, iso-propanol, and n-propanol. The most preferred esters are ethyl acetate and butyl acetate. Other non-limiting examples of suitable organic solvents are benzyl alcohol, amyl acetate, propyl acetate, acetone, heptane, iso-butyl acetate, iso-propyl acetate, toluene, methyl acetate, iso-butanol, n-amyl alcohol, n-butyl alcohol, hexane, and methyl ethyl ketone.

The kits and compositions of the present invention may further comprise information which informs a user of the kit or composition, by words, pictures, and/or the like, that use of the kit or composition will provide one or more long wear benefits, including, but not limited to, resistance to chipping, peeling, denting, and/or peeling.

The films herein are formed when a composition or kit of the present invention is applied to mammalian nails. The films of the present invention comprise one or more layers formed from one or more different compositions, more preferably one, two, or three layers formed from one, two, or three different compositions, respectively, and most preferably two or three layers formed from two or three different compositions, respectively. The preferred films are those which are comprised of a basecoat and a topcoat, and those which further comprise a midcoat.

The films herein form when one or more compositions, as described herein, are applied to and substantially dry on mammalian nails. The compositions useful herein may be described as basecoat compositions, midcoat compositions, or topcoat compositions, depending on their intended positioning on the nail.

A. Basecoat Compositions

As used herein, a "basecoat composition" is a composition which is suitable for application to a mammalian nail to form a basecoat, which is a layer of nail polish. A basecoat composition is preferably applied contiguously to a mammalian nail with or without, more preferably with, one or more succeeding layers applied to the resulting basecoat. The basecoat composition is preferably applied contiguously to a mammalian nail with one or more, more preferably one (topcoat), and most preferably two (midcoat and topcoat), succeeding layers joined to the resulting basecoat.

Without intending to be limited by theory, it is believed that the basecoats of the present invention are beneficial to long wear because they provide preferred surface energy and/or polarity properties, as described herein, which properties result in preferred adhesion of the nail polish to the nail. Such adhesion is believed to be due to physical forces, rather than chemical bonding to the nail. As is known in the art, these physical forces include non-covalent interactions such as polar, non-polar, hydrogen bonding, and charged interactions as well as physical interactions such as mechanical interlocking. Preferably, the basecoat compositions provide one-layer basecoats exhibiting surface energies from about 32 mN/m to about 43 mN/m, more preferably from about 34 mN/m to about 42 mN/m, and/or polarities from about 0.19 to about 0.29, more preferably from about 0.20 to about 0.24.

Without intending to be limited by theory, the surface energies and polarities defined herein are primarily achieved by selection of the film-forming polymer. Formulation adjustments which may change surface energies and/or polarities of the final film may reduce adhesion between the nail surface and the film-forming polymer in the basecoat. Thus, the film-forming polymer itself is selected, first by general class (polyurethiane, polyacryl, e.g.) and second via the chemistry of the monomers present in the film-forming polymer. Preferred polymer classes which achieve the presently defined surface energies and polarities are defined herein. Experimentation within a polymer class, which is well within the purview of the ordinarily skilled artisan, may be utilized to select film-forming polymers having surface energies and polarities which most closely match the defined ranges.

The present basecoat compositions comprise a film-forming polymer, a liquid diluent, and, optionally, one or more other suitable components as described herein. The basecoat compositions preferably comprise from about 0.1% to about 40%, more preferably from about 0.1% to about 20%, still more preferably from about 1% to about 10%, and most preferably from about 2% to about 6% of the film-forming polymer (polymer solids), and preferably at least about 20%, more preferably from about 20% to about 90%, still more preferably from about 40% to about 90%, even more preferably from about 50% to about 90%, and most preferably from about 70% to about 90% of the volatile organic solvent (as described herein above), by weight of the composition. Preferably, the balance of the compositions is substantially water, preferably at least about 4%, more preferably from about 4% to about 80%, still more preferably from about 10% to about 80%, and most preferably from about 25% to about 75%, by weight of the composition, of water.

The film-forming polymers of the basecoat compositions are preferably water-insoluble at ambient temperature and pressure.

Preferred film-forming polymers for use in the basecoat compositions are selected from polyurethanes, polyacryls, polymethacryls, urethane-acryl copolymers, styrene-acryl copolymers, cellulosic polymers, polysiloxanes, and mixtures thereof. The more preferred polymers of basecoat compositions are selected from cellulosic polymers, polyurethanes, polyacryls, polymethacryls, polysiloxanes, and mixtures thereof. Even more preferred polymers of basecoat compositions are selected from polyurethanes, polyacryls, polymethacryls, urethane-acryl copolymers, styrene-acryl copolymers, and mixtures thereof. The most preferred polymers for use in the basecoat compositions are polyturethanes. The most preferred polyurethane for use in basecoat compositions is Sancure 2710® and/or Avalure UR 445®. Preferred types of each of these polymer classes, and examples thereof, are described herein above.

Preferred polyacryls, polymethacryls, and styrene-acryl copolymers for use in the basecoat compositions are those having a glass transition temperature ($T_g$) of from about −30° C. to about +60° C., more preferably from about −20° C. to about +20° C., surface energies from about 32 mJ/m² to about 43 mJ/m², calculated using the harmonic mean equation (as determined by the Wilhelmy Technique described by A. W. Neumann and R. J. Good, *Surface and Colloid Science*, Vol. 2, R. J. Good and R. R. Stromberg, Eds., Plenum Press (1979)), and/or polarities from about 0.19 to about 0.29.

The most preferred polyacryls and polymethacryls for use in basecoat compositions include Glascol LS20, Glascol C37, Joncryl®95, and SCX-1965.

The film-forming polymers of the basecoat compositions are preferably solvent-borne or water-borne, most preferably water-borne. Especially preferred are water-borne polymers selected from polyurethanes, polyacryls, polymethacryls, urethane-acryl copolymers, styrene-acryl copolymers, and mixtures thereof.

B. Topcoat Compositions

As used herein, a "topcoat composition" is a composition which is suitable for application to a mammalian nail to form a topcoat, which is a layer of nail polish. The topcoat composition is preferably applied contiguously to, or applied to, one or more preceding layers. The topcoat composition is more preferably applied contiguously to one or two, preferably one (basecoat), and most preferably two (basecoat and midcoat), preceding layers.

Without intending to be limited by theory, it is believed that the topcoats further benefit long wear because they deflect environmental stressors by virtue of their hardness, toughness, durability, rigidity, and resistance to chipping.

The present topcoat compositions comprise a film-forming polymer, a liquid diluent, and, optionally, other suitable components as described herein.

The film-forming polymers of the topcoat compositions are preferably either solvent-borne or water-borne and are preferably water-insoluble. Preferred film-forming polymers for topcoat compositions have glass transition temperatures ($T_g$) from about +20° C. to about +100° C., more preferably from about +30° C. to about +80° C.

The preferred film-forming polymers of topcoat compositions of the present invention are selected from polyurethanes, polyacryls, polymethacryls, styrene-acryl copolymers, cellulosic polymers, polyesters, vinyl acetate polymers, polysiloxanes, polystyrene-polyacryl mixtures, siloxane-urethane copolymers, polyurethane-polymethacryl mixtures, silicone-acryl copolymers, and mixtures thereof. The more preferred film-forming polymers of topcoat compositions are selected from cellulosic polymers, polyurethanes, polyacryls, polymethacryls, polysiloxanes, and mixtures thereof. Even more preferred film-forming polymers of topcoat compositions are selected from polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof. The most preferred film-forming polymers of topcoat compositions are polyacryls and polyurethane-cellulosic polymer mixtures. The most preferred polyacryl for use in topcoat compositions is Duraplus 2®. Preferred types of each of these polymer classes, and examples thereof, are referred to herein above.

Preferred solvent-borne film-forming polymers include polyurethane-polymethacryl mixtures, polyurethane-cellulosic polymer mixtures, polyurethanes, polyacryls, polymethacryls, silicone-acryl copolymers, and mixtures thereof, more preferably, polyacryls and polyurethane-cellulosic polymer mixtures, and most preferably polyacryls.

Wherein the film-forming polymer of the topcoat composition is solvent-borne, the topcoat composition preferably comprises from about 1% to about 50%, more preferably from about 10% to about 25% of the film-forming polymer (polymer solids), by weight of the composition. The topcoat composition comprising the solvent-borne polymer preferably further comprises from about 50% to about 99%, more preferably from about 75% to about 90%, by weight of the composition, of a volatile organic solvent (as described herein above).

Wherein the topcoat composition comprises a solvent-borne film-forming polymer, preferred optional components include thickeners, plasticizers, pigments or dyes, resins, and slip aids.

Preferred water-borne film-forming polymers are selected from polyurethanes, polyacryls, polymethacryls, styrene-acryl copolymers, siloxane-urethane copolymers, and mixtures thereof. More preferred water-borne film-forming polymers are selected from polyacryls and styrene-acryl copolymers and the most preferred water-borne film-forming polymers are polyacryls.

Wherein the film-forming polymer of the topcoat composition is water-borne, the topcoat composition preferably comprises from about 1% to about 40%, more preferably from about 5% to about 30%, and most preferably from about 10% to about 25%, by weight of the composition, of the film-forming polymer (polymer solids).

The topcoat composition comprising the water-borne polymer preferably further comprises a coalescent. Preferably, the topcoat composition comprising the water-borne polymer comprises from about 0.1% to about 30%, more preferably from about 1% to about 20%, by weight of the composition, of a coalescent. Preferably, the ratio of water-borne film-forming polymer to coalescent is from about 1:1 to about 4:1.

Wherein the topcoat composition comprises a water-borne film-forming polymer, other preferred optional components include plasticizers, slip aids (especially waxes and surfactants containing siloxanes), thickeners, and pigments or dyes. Topcoat compositions comprising water-borne film-forming polymers may also optionally contain up to about 50%, more preferably from about 5% to about 40%, and most preferably from about 10% to about 30%, by weight of the composition of a volatile organic solvent. Preferred organic solvents are described herein above.

Wherein the topcoat composition comprises a water-borne polymer, the balance of the composition is substantially water.

The film-forming polymers of the present topcoat compositions may be cross-linked polymers. The present inventors have surprisingly discovered that film-forming polymers which are cross-linked provide properties which are particularly advantageous for topcoat compositions and topcoats including, for example, chip-resistance and superior hardness. Cross-linking may occur either in the composition itself or after application and film formation. However, as used herein, polymers which are not actually cross-linked in the composition but may become cross-linked (i.e., "cross-linkable" polymers) due to the presence of a basic moiety (as described herein) are referred to herein as cross-linked polymers.

As used herein, a "cross-linked polymer" is a polymer which is ionically linked either intramolecularly to itself and/or intermolecularly to one or more other polymers wherein the linkage is formed through an ionic bridge between a metallic ion and a basic moiety comprising the polymer. Cross-linked polymers are preferably intermolecularly linked. Suitable metallic ions include those with an oxidation state of +2, +3, +4 or higher and which are soluble in water. Preferred metallic ions are selected from $Zn^{+2}$, $Mg^{+2}$, $Ca^{+2}$, $Fe^{+2}$, $Fe^{+3}$, $Al^{+3}$, $Mn^{+2}$, $Co^{+2}$, and $Ni^{+2}$. More preferred metallic ions are selected from $Zn^{+2}$, $Mg^{+2}$, $Ca^{+2}$, $Fe^{+2}$, $Fe^{+3}$, and $Al^{+3}$. The most preferred metallic ion is $Zn^{+2}$.

The basic moieties herein are negatively charged or otherwise basic. The basic moieties may be either present in, or pendant from, the film-forming polymer backbone. Preferred basic moieties are selected from carboxylates, sulfonates, sulfates, phosphates, phosphonates, hydroxymates, borate esters, imidazoles, α-thioketones, thioacids, and alkyl amines. More preferred basic moieties are selected from carboxylates, sulfonates, sulfates, phosphates, phosphonates, and alkyl amines. Even more preferred basic moieties are selected from carboxylates, sulfonates, sulfates, phosphates, and phosphonates. The most preferred basic moieties are carboxylates.

The most preferred cross-linkable polymers are selected from polyacryls, polymethacryls, styrene-acryl copolymers, styrene-methacryl copolymers, and mixtures thereof. Cross-linked polymers may be commercially obtained (for example, Duraplus 2®). Cross-linked polymers may alternatively be produced by obtaining or synthesizing a polymer comprising a pendant basic moiety and adding to that polymer a metal ion solution such as, for example, Zinc Oxide Solution #1 (containing about 15% metal ion solids, commercially available from S.C. Johnson & Sons, Inc.) or Bacote 20 (commercially available from Magnesium Elektron, Inc., Flemington, N.J.). Wherein a metal ion solution is added, the solution is added in an amount sufficient to react substantially completely with the available basic moieties present on the film-forming polymer. Preferably, the amount of metal ion solids, relative to the polymer solids present in the composition, is from about 0.2% to about 0.7%, more preferably from about 0.3% to about 0.6%, and most preferably from about 0.4% to about 0.5%, by weight of the composition.

Wherein the film-forming polymer is cross-linked, the polymer is most preferably water-borne.

Wherein a topcoat comprises a cross-linked polymer, the topcoat may be removed from the nail by a wash treatment with a chelator solution which selectively pulls metal cross-linking ions out of the film and destroys the film. Suitable chelator solutions are selected based on the type of metal ion utilized. Exemplary solutions include, for example, aqueous solutions of ethylenediamine disuccinic acid.

C. Midcoat Compositions

As used herein, a "midcoat composition" is a composition which is suitable for application to a mammalian nail to form a midcoat, which is a layer of nail polish. The midcoat composition is preferably applied contiguously to a preceding layer, either a basecoat or another midcoat, most preferably a basecoat. One or more succeeding layers is applied to the layer formed by the midcoat composition. Preferably, a topcoat is applied contiguously to the layer formed by the midcoat composition.

The use of midcoats is preferred wherein there are significant differences between the physical and/or mechanical properties of the basecoat and the topcoat. For example, midcoats preferably relax stress between flexible basecoats and tough topcoats and/or provide color.

The present midcoat compositions comprise a film-forming polymer, a liquid diluent, and, optionally, other suitable components as described herein. Preferred optional components for midcoat compositions are selected from plasticizers, pigments, and dyes.

Midcoat compositions preferably comprise from about 10% to about 25%, more preferably from about 10% to about 18% of a film-forming polymer, from about 60% to about 85%, more preferably from about 60% to about 80% of a volatile organic solvent (as described herein above), and preferably 0% to about 13%, more preferably from about 5% to about 13%, and most preferably from about 6% to about 12% of a plasticizer, by weight of the composition.

Film-forming polymers comprising the midcoat compositions are selected from cellulosic polymers, polyurethanes, polyacryls, polymethacryls, polysiloxanes, and mixtures thereof. More preferred film-forming polymers are polyacryls and cellulosic polymers, with cellulosic polymers being the most preferred. Preferred types of each of these polymer classes, and examples thereof, are described herein above.

Preferred polyacryls for the midcoat compositions are those which are hydrophobic and/or exhibit a glass-transition temperature ($T_g$) of from about −10° C. to about +30° C. Wherein the polyacryl has a $T_g$ higher than about +30° C., the midcoat composition preferably comprises a plasticizer.

Exemplary compositions suitable for use as midcoat compositions are commercially available such as, for example, those marketed under the Max Factor® or Cover Girl® trade names.

Optional Components

The compositions of the present invention may, independently, comprise additional optional components to enhance their performance as a nail polish. For example, antifoams, buffers, chelating agents, coalescents, dispersing agents, dyes, epoxies, fillers, pigments, preservatives, resins, therapeutic and prophylactic agents, thickeners, wax additives, wetting agents, and the like can be included in the compositions herein. Such optional components may be dispersed, solubilized, or otherwise mixed in the carrier and/or the liquid diluent of the compositions. These components may be added to the compositions herein provided they do not substantially hinder the long wear of the films formed from the compositions and kits. Non-limiting examples of optional components are given below.

Coalescents

Coalescents may optionally be added to the compositions to enhance film-formation, most preferably wherein the film-forming polymer is water-borne. Such coalescing aids are known in the art and are typically glycol ethers or glycol ether esters such as $C_{1-10}$ straight or branched chain alkyl glycol alkyl ethers, $C_{1-10}$ straight or branched chain alkyl ether acetates, di-$C_{1-10}$ alkyl ether acetates, and $C_{1-1}$ alkyl glycol phenyl ethers. Preferred coalescing aids include, for example, ethylene glycol ethers (e.g., Dowanol EB®, commercially available from Dow Chemical Co.), diethylene glycol ethers, triethylene glycol ethers, propylene glycol ethers (e.g., Dowanol PnP®, Dow Chemical Co.), dipropylene glycol ethers (e.g., Dowanol DPnP®, Dow Chemical Co.), tripropylene glycol ethers, terpenes, camphor, methyl cellusolve, butyl cellusolve, hexyl cellusolve, methyl carbitol, butyl carbitol, and dibutyl phthalate.

Preferably, a composition comprises from 0% to about 10%, more preferably from about 0.1% to about 10%, by weight of the composition, of a coalescent.

Pigments or Dyes

Pigments and other suitable coloring agents, such as dyes, may be incorporated into the compositions. Suitable pigments are inorganic or organic pigments known as, for example, the FD&C and D&C colors, lakes, and iron oxides. Such pigments are disclosed in the C.T.F.A. *Cosmetic Ingredient Handbook*, First Edition, 1988. Organic pigments include, for example, D and C Red, Nos. 10, 11, 12, and 13, D and C Red No. 7, D and C Red Nos. 5 and 6, D and C Red Nos. 30 and 34, lacquers such as D and C Yellow No. 5 and D and C Red No. 2, and guanine. Inorganic pigments include, for example, titanium dioxide, bismuth oxychloride, brown iron oxide, and the red iron oxides.

Preferably, the present compositions comprise from 0% to about 5%, more preferably from 0% to about 2%, and most preferably from 0% to about 1%, by weight of the composition, of a pigment or dye.

Plasticizers

Without intending to be limited by theory, plasticizers cause a composition to become more easily deformed. One or more plasticizers may optionally be added to the present compositions. Suitable plasticizers include those disclosed in WO 97/00664, Chen et al, assigned to Eastman Chemical Co. Suitable plasticizers include phthalates, nonionic surfactant polymers, camphor, castor oil, sucrose acetate isobutyrate, alkyl toluenesulfonamides, e.g., ethyl toluenesulfonamide (e.g., Uniplex PX-45, commercially available from Unitex Chemical Corp., Greenboro, N.C.), and polyester acid derivatives (e.g., Uniplex 670P, commercially available from Unitex Chemical Corp.), particularly polyester di- and tri-acids. Preferred plasticizers include diethyl phthalate, dibutyl phthalate, dioctyl plithalate, diethyl tartrate, dibutyl tartrate, diethyl phosphate, dibutyl phosphate, polyester sebacates, such as Paraplex G-25® (commercially available from C. P. Hall, Bedford Park, Ill.) polyester adipates, such as Paraplex G-50® (C. P. Hall) and tetraethylene glycol di-2-ethylhexoate, available as Tegmer® (C. P. Hall). The most preferred plasticizers include dibutyl phthalate, Paraplex G-25®, Paraplex G-50®, camphor, Uniplex PX-45, and Tegmer®.

A composition preferably comprises from 0% to about 15%, more preferably from 0% to about 10%, and most preferably from 0% to about 5%, by weight of the composition, of a plasticizer.

Preservatives

One or more preservatives may optionally be added to the present compositions to prevent, inhibit, or retard microbial growth in the composition. Preferred preservatives include methyl paraben, ethyl paraben, propyl paraben, benzyl alcohol, benzoic acid, benzoates (preferably sodium benzoate), sorbates (preferably potassium sorbate), sodium dehydroacetate, 1-(3-chloroallyl)-3,5,7-triaza-1-azoniaadamantane chloride (which may be obtained commercially as Quaternium-15® from Dow Chemical Co., Midland, Mich.), a mixture of 95% 1,3-dimethylol-5,5-dimethyl hydantoin and 5% 3-iodo-2-propynyl butyl carbamate (which mixture is commercially available as Glydant Plus® from Lonza, Inc., Fair Lawn, N.J.), 1,3-dimethylol-5,5-dimethyl hydantoin (commercially available as Glydant® from Lonza, Inc.), diazolidinyl urea (commercially available as Germall II® from Sutton Laboratories, Chatham, N.J.), imidazolidinyl urea (commercially available as Germall 115® from Sutton Laboratories), phenoxyethanol, and Kathon® (commercially available from Rohm and Haas Co., Philadelphia, Pa.). The most preferred preservatives include methyl paraben, ethyl paraben, propyl paraben, benzyl alcohol, benzoic acid, benzoates (preferably sodium benzoate), sorbates (preferably potassium sorbate), and sodium dehydroacetate.

A composition preferably comprises from 0% to about 10%, more preferably from 0% to about 5%, and most preferably from 0% to about 1%, by weight of the composition, of a preservative.

Resins

Resins including, for example, epoxies and polyacrylics, may optionally be added. Examples of suitable resins include Polytex E75® (commercially available from Estron Chemical, Inc., Calvert City, Ky.) and Acryloid B66® (commercially available from Rohm and Haas, Philadelphia, Pa.).

A composition preferably comprises from 0% to about 15%, more preferably from about 0.5% to about 10%, by weight of the composition, of a resin.

Slip Aids

Slip aids may optionally be added to improve surface friction, water resistance, abrasion resistance, and mechanical properties. Slip aids which may be used include wax additives including, for example, animal, fossil, vegetable, mineral, or synthetic waxes. Preferred wax additives include beeswax, carob, candelilla, ozocerite, polyethylene waxes, paraffin waxes, polypropylene waxes, polytetrafluoroethylene (commercially available as Teflon® from DuPont, Wilmington, Del.), nylons, and polyamides. Specifically, preferred wax additives include, but are not limited to, Jonwax® 26 (commercially available from S.C. Johnson Polymer, Sturtevant, Wis.) Jonwax® 120 (S.C. Johnson Polymer), Chemcor 325N35, Chemcor 43N40, Glaswax® E-1 (commercially available from Allied Colloids, Suffolk, Va.), Glaswax® E-1235 (Allied Colloids), Drewax® E-3030 (commercially available from Ashland Chemical, Boontown, N.J.), Drewax® E-7030 (Ashland Chemical), Lanco® PP1362D (commercially available from Lubrizol, Wichliffe, Ohio), Lanco® A1601 (Lubrizol), and Lanco® TF1780 (Lubrizol).

Other slip aids include materials containing silicone such as copolymers of polyether and polysiloxane. Examples of such slip aids include, for example, Glide 450 and Abil B-8830 (both of which are commercially available from Goldschmidt Chemical, Hopewell, Va.).

The present compositions preferably comprise from 0% to about 10%, more preferably from about 0.1% to about 10%, even more preferably from about 0.5% to about 8%, and most preferably from about 0.5% to about 3% of a slip aid.

Stabilizers

One or more stabilizers may be added to the compositions herein, e.g., to prevent pigment from settling or to achieve desired application properties. Preferably, stabilizers are added to compositions comprising a solvent-borne film-forming polymer. Preferred stabilizers include clays, e.g., organically modified bentonites and hectorites such as stearalkonium bentonite and stearalkonium hectorite (commercially available from Rheox, Inc., Hightstown, N.J.).

Wherein a stabilizer is added, the composition preferably comprises from about 0.25% to about 3%, still more preferably from about 0.25% to about 2.5%, and most preferably from about 1% to about 2% of the stabilizer, by weight of the composition.

Therapeutic and Prophylactic Agents

Therapeutic and/or prophylactic agents such as, for example, vitamins, proteins, anti-fungal and anti-microbial agents, and sunscreens (including UV-A, UV-B, and broad spectrum solar filters) may optionally be added to the present compositions for the further care and protection of the nails.

Thickeners

Thickeners may optionally be added to the compositions and films herein to achieve desired rheology and application properties. Preferably, thickeners are utilized wherein the composition comprises a water-borne film-forming polymer or at least 4% water. Preferred thickeners include hydroxyethyl cellulose, hydroxypropyl cellulose, methyl cellulose, and other conventional cellulosic polymers, associative thickeners (e.g., hydrophobically modified cellulosic polymers, nonionic urethanes, and alkali swellable urethanes) including Aculyn® 44 (commercially available from Rohm & Haas, Philadelphia, Pa.), clays (e.g., laponite and hydrophilic montmorillonite (commercially available as Bentone® from Rheox, Hightstown, N.J.), and natural rubbers and gums (e.g., guar gum, quaternized guar gum sold under the name Jaguar® C-13-S by Rhone-Poulenc, Shelton, Conn.), hydroxypropyl guar gum, gum arabic, carob gum, carrageenan, and xanthan gum).

The present compositions preferably comprise from 0% to about 10%, more preferably from about 0.1% to about 10%, and even more preferably from about 0.1% to about 5% of a thickener, by weight of the composition.

Preferred Kits of the Present Invention

The kits herein are comprised of two or more separate and different compositions, most preferably two or three separate and different compositions. Preferably, the kits are comprised of at least one of a basecoat composition, a midcoat composition, and/or a topcoat composition. More preferably, the kits are comprised of a basecoat composition, a topcoat composition, and, optionally, a midcoat composition.

A preferred kit ("Kit 1") having two separate and different compositions comprises a basecoat composition and a topcoat composition. The basecoat composition of Kit 1 comprises a film-forming polymer, preferably a water-insoluble polymer, which is selected from polyurethanes, polyacryls, polymethacryls, urethane-acryl copolymers, styrene-acryl copolymers, and mixtures thereof. The topcoat composition of Kit 1 comprises a film-forming polymer, preferably a water-insoluble polymer, which is selected from polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

Another preferred kit ("Kit 2") having three separate and different compositions comprises the basecoat composition and topcoat composition as described for Kit 1, and further comprises a midcoat composition. The midcoat composition of Kit 2 comprises a film-forming polymer, preferably a water-insoluble polymer, which is selected from cellulosic polymers, polyurethanes, polyacryls, polymethacryls, polysiloxanes, and mixtures thereof.

Another preferred kit ("Kit 3") having two separate and different compositions comprises a basecoat composition and a topcoat composition. The basecoat composition of Kit 3 comprises a film-forming polymer, preferably a water-insoluble polymer, which is selected from polyurethanes, polyacryls, polymethacryls, urethane-acryl copolymers, styrene-acryl copolymers, and mixtures thereof. The topcoat composition of Kit 3 comprises a film-forming polymer, preferably a water-insoluble polymer, which is selected from cellulosic polymers, polyurethanes, polyacryls, polymethacryls, polysiloxanes, and mixtures thereof.

Another preferred kit ("Kit 4") having two separate and different compositions comprises a basecoat composition and a topcoat composition. The basecoat composition of Kit 4 comprises a film-forming polymer, preferably a water-insoluble polymer, which is selected from cellulosic polymers, polyurethanes, polyacryls, polymethacryls, polysiloxanes, and mixtures thereof. The topcoat composition of Kit 4 comprises a film-forming polymer, preferably a water-insoluble polymer, selected from polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

Method of Making and Using

The compositions of the present invention are made using conventional formulation and mixing techniques. A layer of nail polish may be prepared by standard application of a composition to mammalian nails using a standard brush-applicator as is commonly utilized in the art and removing sufficient liquid diluent (through evaporation of volatiles, most preferably at ambient pressures and temperatures) to form the substantially dry layer. The multi-layer films of the present invention are prepared in a similar manner by standard application of one or more additional compositions contiguously to the preceding layer. Such application is well-known in art.

The present invention includes a method of coating mammalian nails with a nail polish film, wherein the film comprises one or more layers. The method comprises the steps of:

(i) applying a basecoat composition contiguously to the nail, wherein the basecoat composition comprises a film-forming polymer and a liquid diluent;

(ii) removing sufficient liquid diluent from the basecoat composition to form a substantially dry basecoat;

(iii) optionally applying a midcoat composition to the basecoat, wherein the midcoat composition comprises a film-forming polymer and a liquid diluent;

(iv) removing sufficient liquid diluent from the midcoat composition to form a substantially dry layer;

(v) optionally applying a topcoat composition to the basecoat (or the layer formed by the midcoat composition, if used), wherein the topcoat composition comprises a film-forming polymer and a liquid diluent; and (vi) removing sufficient liquid diluent from the topcoat composition to form a substantially dry topcoat;

wherein the basecoat exhibits a surface energy from about 32 mN/m to about 43 mN/m, more preferably from about 34 mN/m to about 42 mN/m, and/or a polarity from about 0.19 to about 0.29, more preferably from about 0.20 to about 0.24.

Properties of Films of the Present Invention

The present kits and compositions provide films having defined adhesive properties which are expressed by their surface energies and polarities.

Surface energy is a critical parameter for ensuring and predicting adhesion between a nail polish and a mammalian nail. The present inventors have discovered that films will best adhere to the nail if the surface energy of the film matches, or nearly matches, the surface energy and/or polarity of the nail. The present inventors have surprisingly discovered compositions providing one-layer films which exhibit surface energies from about 32 mN/m to about 43 mN/m, more preferably from about 34 mN/m to about 42 mN/m, and/or polarities from about 0.19 to about 0.29, more preferably from about 0.20 to about 0.24.

Surface Energy and Polarity Method

The following symbols and terms are used in the method herein:

$\gamma_s = \gamma_s^d + \gamma_s^p$ for test nail polish=surface energy of test nail polish, wherein:

$\gamma_s^d$=dispersive component of $\gamma_s$ $\gamma_s^p$=polar component of $\gamma_s$ $$X^P = \frac{\gamma_s^p}{\gamma_s} = \text{polarity} \quad \text{(equation 1)}$$

Similarly, $\gamma_L = \gamma_L^d + \gamma_L^p$ for liquid=surface tension of a liquid, wherein:

$\gamma_L^d$=dispersive component of $\gamma_L$ $\gamma_L^p$=polar component of $\gamma_L$ Surface energy measurements are made by the Wilhelmy technique (described in A. W. Neumann and R. J. Good, *Surface and Colloid Science*, Vol. 2, R. J. Good and R. R. Stromberg, Eds., Plenum Press (1979)), a Krüss K12 tensiometer, and K121 software which is available from Krüss USA, Charlotte, N.C. (or equivalents thereof). All measurements are performed at 22° C. +/−2° C. In this method, a platinum plate or a cover slip coated with the test nail polish is suspended from a balance which measures weight in grams to ten thousandths of a gram. Each test liquid (separately, water and methylene iodide) has its own glass reservoir which is placed on top of a motorized platform allowing the test liquid to be brought into contact with the platinum plate or solid sample of interest, and is suspended from the balance overhead. The liquids are each introduced to a reservoir at a depth of about 1 cm.

To verify cleanliness of the reservoir and purity of the test liquid, the surface tension of each liquid in its respective reservoir is measured and checked versus literature values. With the platinum plate in place, the "Plate Method" is selected from the Kruiss software. This method raises the platform until it determines the location of the plate-liquid interface (determined by the platform height at which the balance detects an increase of 0.001 gram). The platform then further raises 1 mm past this point, then returns to the height denoting the interface. At this point, one balance reading is taken each second for 10 seconds. The software displays the surface tension calculated by:

$$\gamma_L = \frac{F}{L_w \cos\theta} \quad \text{(equation 2)}$$

wherein F=wetting force (measured by balance); $L_w$=wetted length (the perimeter of the plate); and θ=contact angle (assigned a value of 0 for liquids against platinum).

Glass cover slips are attached to a level surface with Scotch® tape and the nail polish to be tested (test nail polish) is applied to one half of the top side of the cover slip in a similar manner to standard application of one layer of a nail polish composition to the nail. The test nail polish is allowed to dry at ambient temperature for at least one hour. The cover slip is then turned over and once again attached to the level surface Scotch® tape in such a manner that the polish does not come in contact with any surface. The test nail polish is applied to the second side of the cover slip in a similar manner and allowed to dry at ambient temperature for at least one hour. The test nail polish is then further dried in a convection oven at 87° F. Six cover slips are prepared for each polish to be tested. Measurements are taken on the prepared slips no sooner than 24 hours after application of the polish to the second side of the cover slip.

Once the slips and test liquids have been prepared as described above, the width and thickness of each nail polish film is measured using a digital vernier calipers to the nearest 0.01 mm. These measurements are used to determine the perimeter (P) (the "wetted length" in accordance with the nomenclature used by Krüss) according to the following equation:

$$P = (2*\text{Width}) + (2*\text{Thickness})$$

The width and thickness are inputs into the Krüss software, which performs calculation of the perimeter following the above formula.

A prepared slip is mounted in a holding clip and suspended from the balance. The Krüss software controlling the instrument raises the motorized platform holding the probe liquid reservoir (platform speed of 1.2 mm/min) until the balance detects a change in weight of 0.001 g. The height corresponding to this weight is denoted the interface height. The platform speed is decreased to 60% of its original speed, and data collection (readings from the balance) is commenced. After raising the platform to 3 mm beyond the height of the interface such that the liquid contacts the film on the slip, the platform stops, waits one second, then reverses direction, collecting data throughout, until the sample pulls completely free of the probe liquid. The data collected as the platform rises is used to determine the advancing contact angle, while that data collected as the platform recedes is used to determine the receding contact angle. The software calculates both of these angles by performing a linear regression to each the "advancing" data and "receding" data plotted as force vs. depth. The total force measured by the balance is a sum of the wetting force (F as given in equation (2) above) and the buoyancy force, which is a function of immersion depth. The buoyancy force is given by the slope of the linear regression and the wetting force is given by the y-intercept. Using the y-intercept and equation (1), the advancing and receding contact angles are calculated. Advancing angles are always greater than or equal to the receding angle. Advancing angles from measurements in both water and methylene iodide are used in calculating the surface energy of the test nail polish film. Three of the six prepared slips for each nail polish are used to measure the contact angle of water on the test substrate. The remaining three prepared slips are used to measure the contact angle of methylene iodide on the test substrate.

For each test nail polish, the three advancing water contact angle values are averaged, and the three methylene iodide advancing contact angle values are also averaged. These average contact angles for each of the two probe liquids are used to determine the surface energy of the substrate.

Relation of interfacial tensions to contact angles is as follows:

$$\gamma_L \cos\theta = \gamma_S - \gamma_{SL}$$

where $\gamma_{SL}$ = solid-liquid interfacial tension (equation 3)

and all others have the same definitions as given above. The Harmonic Mean equation, $$\gamma_{SL} = \gamma_S + \gamma_L - 4\frac{\gamma_S^d \gamma_L^d}{\gamma_S^d + \gamma_L^d} - 4\frac{\gamma_S^p \gamma_L^p}{\gamma_S^p + \gamma_L^p}, \quad \text{(equation 4)}$$

provides a method for relating the solid-liquid interfacial tension to the individual solid and liquid surface energies and their dispersive and polar components (defined above). The equation used to calculate surface energies is obtained by combining equations (3) and (4), to get:

$$\gamma_L \cos\theta = -\gamma_L + 4\frac{\gamma_S^d \gamma_L^d}{\gamma_S^d + \gamma_L^d} + 4\frac{\gamma_S^p \gamma_L^p}{\gamma_S^p + \gamma_L^p}, \quad \text{(equation 5)}$$

Using equation 4, the known liquid surface tension as well as the dispersive and polar components for each probe liquid, and the experimentally determined contact angle, a system of 2 equations and 2 unknowns is obtained. Solving equations 4 and 5 simultaneously gives $\gamma_S^d$ and $\gamma_S^p$, the dispersive and polar components of the test nail polish film's surface energy, respectively. These two values sum to give the total surface energy, $\gamma_S$. The polarity, $x^p$, is calculated by equation (1), above.

Values used for liquid surface tension and its components for each test liquid are given in the table below:

| Test Liquid | $\gamma_L$/mN/m | $\gamma_L^d$/mN/m | $\gamma_L^p$/mN/m |
|---|---|---|---|
| water | 72.3 | 18.7 | 53.6 |
| iodomethane | 50.8 | 48.5 | 2.3 |

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

In the examples herein below, all polymer component percentages are expressed in weight percent of solid polymer (based on the total composition).

Examples 1A–1H
The compositions of Examples 1A–1H are representative of basecoat compositions of the present invention:

| | Ex. 1A | Ex. 1B | Ex. 1C | Ex. 1D | Ex. 1E | Ex. 1F | Ex. 1G | Ex. 1H |
|---|---|---|---|---|---|---|---|---|
| Sancure 2710 ® | 5.5% | 4% | 5.81% | 5.81% | 5.4% | — | 5.74% | 5.74% |
| Glascol LS20 ® | — | — | — | — | 5.7% | — | — | — |
| NeoRez R967 ® | — | — | — | — | — | 5.87% | — | — |
| Ethanol | 7.9% | — | — | — | — | — | — | — |
| iso-Propanol | — | — | — | 32.13% | 44.9% | 65.8% | 65.83% | 46.99% |

-continued

Examples 1A–1H
The compositions of Examples 1A–1H are
representative of basecoat compositions of the present invention:

|  | Ex. 1A | Ex. 1B | Ex. 1C | Ex. 1D | Ex. 1E | Ex. 1F | Ex. 1G | Ex. 1H |
|---|---|---|---|---|---|---|---|---|
| Ethyl Acetate | 78.1% | — | — | — | — | — | — | — |
| n-Propanol | — | 71.6% | 70% | — | — | — | — | — |
| Methyl Paraben | — | — | 0.1% | 0.21% | — | 0.1% | 0.2% | 0.2% |
| Propyl Paraben | — | — | 0.1% | — | 0.2% | — | — | — |
| Water | 8.5% | 24.4% | 24% | 61.85% | 43.8% | 28.23% | 28.23% | 47.07% |

Examples 2A–2E
The compositions of Examples 2A–2E are representative
of topcoat compositions of the present invention:

|  | Ex. 2A | Ex. 2B | Ex. 2C | Ex. 2D | Ex. 2E |
|---|---|---|---|---|---|
| Duraplus 2 ® | 21% | — | — | 21% | — |
| Nitrocellulose RS ¼ second | — | 15% | — | — | 6.75 % |
| Sanres ®EX499 | — | 3.6% | — | — | — |
| Sanres ®12711 | — | 1.5% | 15.5% | — | — |
| Sanres ®6012 | — | — | — | — | 8.25% |
| Surcol ®441 | — | — | 4.5% | — | — |
| Dowanol DPnP ® | 10% | — | — | 10% | — |
| Dibutyl Phthalate | 3.9% | — | — | 1.6% | — |
| Glide 450 ® | 0.3% | — | — | 0.3% | — |
| Aculyn 44 ® | 0.5% | — | — | — | — |
| Polytex E-75 | — | 1% | — | — | — |
| Drewax E-3030 ® | — | — | — | 1.2% | — |
| Paraplex G-50 ® | — | 7.6% | — | — | — |
| Butyl Acetate | — | 32.9% | 30% | — | 40% |
| Ethyl Acetate | — | 27.4% | 10% | — | — |
| iso-Propanol | — | 11% | 30% | — | 35% |
| Toluene | — | — | — | — | 10% |
| Acetone | — | — | 10% | — | — |
| Water | 64.3% | — | — | 65.9% | — |

Example 3
The following composition may be used as either a midcoat
composition or a topcoat composition.

| Component | Supplier Slurry Code* | Source | Percentage |
|---|---|---|---|
| Solid Nitrocellulose RS ¼ second (available as a slurry) | 50-C3-690 | Akzo Nobel, Somerset, NJ | 7.05% |
| Solid Nitrocellulose RS ½ second (available as a slurry) | 5528 | Scholle Corp., College Park, GA | 7.00% |
| Clay** (available as a slurry) | Bentone slurry | Kirker Enterprises Inc., Paterson, NJ | 1.04% |
| Red #7 Solid (available as a slurry) | Red #7 slurry 6R381 | Penn Color, Doylestown, PA | 0.60% |
| Butyl Acetate |  | J.T. Baker, Phillipsburg, NJ | 27.77% |
| Ethyl Acetate |  | J.T. Baker, Phillipsburg, NJ | 24.00% |
| iso-Propanol |  | J.T. Baker, Phillipsburg, NJ | 6.55% |
| Uniplex 600 |  | Unitex, Greensboro, NC | 11.12% |
| Toluene |  | E.M. Science, Gibbstown, NJ | 6.44% |
| Camphor |  | Universal Preservachem, Edison, NJ | 1.43% |
| Dibutyl Phthalate |  | Eastman Kodak, Kingsport, TN | 7.00% |
| Total |  |  | 100% |

The slurries contain, in addition to the component indicated, components which are listed in the above formula (such as, for example, butyl acetate and iso-propanol). The percentage given for each component is the percentage of that component only (for example, Solid Nitrocellulose RS ¼ second is present in the control formula at a solids level of 7.05%, exclusive of other components). The levels of the other components in each slurry are combined and reflected in the formula given above. For example, the levels of butyl acetate in Nitrocellulose RS ¼ second slurry, Nitrocellulose RS ½ second slurry, clay, and Red #7 Solid are combined and reflected in the percentage given for the butyl acetate component. **Clay is 50/50 (weight percent ratio) stearalkonium hectorite/stearalkonium bentonite solids.

The composition of Example 3 may be prepared as follows. Weigh all components together into a sealable jar to hold a 100 gram batch with minimal head-space. Add six stainless steel balls, each of which are 3/16 inches in diameter. Mix on a conventional paint shaker for thirty minutes. Transfer to conventional nail polish bottles.

Example 4

A kit comprising two separate nail polish compositions is prepared. The compositions are a fast-drying basecoat composition of Example 1 and a topcoat composition which is a conventional nail polish such as Max Factor® International (comprising butyl acetate, ethyl acetate, nitrocellulose, toluenesulphonamide formaldehyde resin, dibutyl phthalate, toluene, iso-propanol, camphor, benzophenone, stearalkonium hectorite, and polyester resin). The basecoat composition is applied contiguously to mammalian nails using a standard brush-applicator. A basecoat is allowed to form. The topcoat composition is applied contiguously to the basecoat using a standard brush-applicator. The topcoat composition is allowed to form a topcoat over a five minute time period, resulting in a film having two layers.

Example 5

A kit comprising two separate nail polish compositions is prepared. The compositions are a basecoat composition of Example 1 and a topcoat composition of Example 2. The basecoat composition is applied contiguously to mammalian nails using a standard brush-applicator. A basecoat is allowed to form over a period of five minutes. The topcoat composition is applied contiguously to the basecoat using a standard brush-applicator. The topcoat composition is allowed to form a topcoat over a five minute time period, resulting in a film having two layers.

Example 6

A kit comprising two separate nail polish compositions is prepared. The compositions are a basecoat composition of Example 1 and a topcoat composition which is a conventional nail polish such as Max Factor® International (comprising butyl acetate, ethyl acetate, nitrocellulose, toluenesulfonamide formaldehyde resin, dibutyl phthalate, toluene, iso-propanol, camphor, benzophenone, stearalkonium hectorite, and polyester resin). The basecoat composition is applied contiguously to mammalian nails using a standard brush-applicator. A basecoat is allowed to form over a period of five minutes. The topcoat composition is applied contiguously to the basecoat using a standard brush-applicator. The topcoat composition is allowed to form a topcoat over a five minute time period, resulting in a film having two layers.

Example 7

A kit comprising three separate nail polish compositions is prepared. The compositions are a basecoat composition of Example 1, a midcoat composition which is a conventional nail polish, such as Max Factor® International (comprising butyl acetate, ethyl acetate, nitrocellulose, toluenesulfonamide formaldehyde resin, dibutyl phthalate, toluene, iso-propanol, camphor, benzophenone, stearalkonium hectorite, and polyester resin) and a topcoat composition of Example 2. The basecoat composition is applied contiguously to mammalian nails using a standard brush-applicator. A basecoat is allowed to form over a period of five minutes. The midcoat composition is applied contiguously to the basecoat using a standard brush-applicator. The midcoat composition is allowed to form a layer over a period of five minutes, resulting in a film having two layers. The topcoat composition is applied contiguously to the layer formed from the midcoat composition using a standard brush-applicator. The topcoat composition is allowed to form a topcoat over a period of five minutes, providing a film having three layers.

Example 8

A kit comprising two separate nail polish compositions is prepared. The compositions are a basecoat composition of Example 1 and the topcoat composition as set forth in Example 3. The basecoat composition is applied contiguously to mammalian nails using a standard brush-applicator. A basecoat is allowed to form. The topcoat composition is applied contiguously to the basecoat using a standard brush-applicator. The topcoat composition is allowed to form a topcoat over a five minute time period, resulting in a film having two layers.

What is claimed is:

1. A composition suitable for use as a nail polish for mammalian nails comprising:
    (a) a film-forming polymer; and
    (b) a carrier comprising at least about 4% of water and at least about 20% of a volatile organic solvent;
wherein the composition when applied to the nail forms a one-layer film exhibiting a surface energy from about 32 mN/m to about 43 mN/m and a polarity from about 0.19 to about 0.29.

2. A composition according to claim 1 wherein the carrier comprises from about 10% to about 80% of water.

3. A composition according to claim 2 wherein the polymer is a water-insoluble polymer selected from the group consisting of polyurethanes, polyacryls, polymethacryls, urethane-acryl copolymers, styrene-acryl copolymers, and mixtures thereof.

4. A composition according to claim 3 wherein the polymer is a polyurethane.

5. A composition according to claim 2 wherein the surface energy is from about 34 mN/m to about 42 mN/m and the polarity is from about 0.20 to about 0.24.

6. A one-layer film prepared by the process of applying to mammalian nails a composition according to claim 2.

7. A film according to claim 6 wherein the polymer is a water-insoluble polymer selected from the group consisting of polyurethanes, polyacryls, polymetliacryls, urethane-acryl copolymers, styrene-acryl copolymers, and mixtures thereof.

8. A film according to claim 7 wherein the polymer is a polyurethane.

9. A film according to claim 6 wherein the surface energy is from about 34 mN/m to about 42 mN/m and the polarity is from about 0.20 to about 0.24.

10. A kit suitable for use as a nail polish for mammalian nails, the kit comprising two or more different compositions wherein each composition comprises a film-forming polymer and a carrier, wherein at least one of the compositions comprises at least about 4% water and at least about 20% of a volatile organic solvent which when applied to the nail forms a one-layer film exhibiting a surface energy from about 32 mN/m to about 43 mN/m and a polarity from about 0.19 to about 0.29.

11. A kit according to claim 10 wherein one of the compositions is a basecoat composition and wherein the basecoat composition when applied to the nail forms the one-layer film.

12. A kit according to claim 11 wherein the film-forming polymer of the basecoat composition is a water-insoluble polymer selected from the group consisting of polyurethanes, polyacryls, polymethacryls, urethane-acryl copolymers, styrene-acryl copolymers, copolymers of any of the foregoing polymers, and mixtures thereof.

13. A kit according to claim 12 wherein the water-insoluble polymer is a polyurethane.

14. A kit according to claim 11 comprising the basecoat composition and a topcoat composition wherein:
    (a) the film-forming polymer of the basecoat composition is a water-insoluble polymer selected from the group consisting of polyurethanes, polyacryls, polymethacryls, urethane-acryl copolymers, styrene-acryl copolymers, and mixtures thereof; and
    (b) the topcoat composition comprises a film-forming water-insoluble polymer selected from the group consisting of polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

15. A kit according to claim 11 comprising the basecoat composition and a topcoat composition wherein:
    (a) the film-forming polymer of the basecoat composition is a water-insoluble polymer selected from the group consisting of polyurethanes, polyacryls, polymethacryls, urethane-acryl copolymers, styrene-acryl copolymers, and mixtures thereof; and
    (b) the topcoat composition comprises a film-forming water-insoluble polymer selected from the group consisting of selected from the group consisting of cellulosic polymers, polyurethanes, polyacryls, polymethacryls, polysiloxanes, and mixtures thereof.

16. A kit according to claim 14 further comprising a midcoat composition comprising a film-forming water-insoluble polymer selected from the group consisting of cellulosic polymers, polyurethanes, polyacryls, polymethacryls, polysiloxanes, and mixtures thereof.

17. A kit according to claim 10 wherein the surface energy is from about 34 mN/m to about 42 mN/m and the polarity is from about 0.20 to about 0.24.

18. A kit according to claim 10 further comprising information that use of the kit provides one or more long wear benefits.

19. A film prepared by the process of:
(i) applying a basecoat composition suitable for use as a nail polish for mammalian nails contiguously to the nail, wherein the basecoat composition comprises a film-forming polymer and a liquid diluent comprising at least about 4% water and at least about 20% of a volatile organic solvent;
(ii) removing sufficient liquid diluent from the basecoat composition to form a substantially dry basecoat;
(iii) applying a topcoat composition to the nail, wherein the topcoat composition comprises a film-forming polymer and a liquid diluent; and
(iv) removing sufficient liquid diluent from the topcoat composition to form a substantially dry topcoat;
wherein the basecoat exhibits a surface energy from about 32 mN/m to about 43 mN/m and a polarity from about 0.19 to about 0.29.

20. A film according to claim 19 wherein:
(a) the film-forming polymer of the basecoat composition is a water-insoluble polymer selected from the group consisting of polyurethanes, polyacryls, polymethacryls, urethane-acryl copolymers, styrene-acryl copolymers, and mixtures thereof, and
(b) the film-forming polymer of the topcoat composition is a water-insoluble polymer selected from the group consisting of polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

21. A film according to claim 19 wherein:
(a) the film-forming polymer of the basecoat composition is a water-insoluble polymer selected from the group consisting of polyurethanes, polyacryls, polymethacryls, urethane-acryl copolymers, styrene-acryl copolymers, and mixtures thereof; and
(b) the film-forming polymer of the topcoat composition is a water-insoluble polymer selected from the group consisting of cellulosic polymers, polyurethanes, polyacryls, polymethacryls, polysiloxanes, and mixtures thereof.

22. A film according to claim 20 further prepared by the steps comprised of:
(v) applying a midcoat composition contiguously to the basecoat, wherein the midcoat composition is comprised of a film-forming polymer and a liquid diluent, wherein the film-forming polymer of the midcoat composition is selected from the group consisting of cellulosic polymers, polyurethanes, polyacryls, polymetliacryls, polysiloxanes, and mixtures thereof; and
(vi) removing sufficient liquid diluent from the midcoat composition to form a substantially dry layer;
wherein the topcoat composition is applied contiguously to the layer formed by the midcoat composition.

23. A method of coating mammalian nails with a nail polish film, the film comprising two or more layers, wherein the method comprises the steps of:
(i) applying a basecoat composition contiguously to the nail, wherein the basecoat composition comprises a film-forming polymer and a liquid diluent comprising at least about 4% water and at least about 20% of a volatile organic solvent;
(ii) removing sufficient liquid diluent from the basecoat composition to form a substantially dry basecoat;
(iii) applying a topcoat composition to the nail, wherein the topcoat composition comprises a film-forming polymer and a liquid diluent; and
(iv) removing sufficient liquid diluent from the topcoat composition to form a substantially dry topcoat;
wherein the basecoat exhibits a surface energy from about 32 mN/m to about 43 mN/m and a polarity from about 0.19 to about 0.29.

* * * * *

UNITED STATES PATENT AND TRADEMARK OFFICE
CERTIFICATE OF CORRECTION

PATENT NO.    : 6,306,375 B1
DATED         : October 23, 2001
INVENTOR(S)   : Ellingson et al.

It is certified that error appears in the above-identified patent and that said Letters Patent is hereby corrected as shown below:

Column 4,
Line 33, "polyurethane-polymetliacryl" should read -- polyurethane-polymethacryl --.
Line 43, "Druapluse®" should read -- Duraplus® --.

Column 5,
Line 12, "polytireltlhanes" should read -- polyurethanes --.
Lines 56 and 57, " polyuretlianes" should read -- polyurethanes --.
Line 57, "2060and" should read -- 2060 and --.
Line 62, "UR 4451®" should read -- UR 455® --.

Column 7,
Line 18, "(polyurethiane," should read -- (polyurethane, --.
Line 61, "polyturethanes" should read -- polyurethanes --.

Column 11,
Line 49, "$C_{1-1}$" should read -- $C_{1-10}$ --.

Column 12,
Line 10, "I%" should read -- 1% --.
Line 26, "plithalate" should read -- phthalate --.

Column 16,
Line 41, "Kruiss" should read -- Krüss --.

Column 22,
Line 8, "polymetliacryls" should read -- polymethacryls --.

UNITED STATES PATENT AND TRADEMARK OFFICE
CERTIFICATE OF CORRECTION

PATENT NO. : 6,306,375 B1
DATED : October 23, 2001
INVENTOR(S) : Ellingson et al.

It is certified that error appears in the above-identified patent and that said Letters Patent is hereby corrected as shown below:

Column 24,
Line 16, "polymetliacryls" should read -- polymethacryls --.

Signed and Sealed this

Tenth Day of December, 2002

JAMES E. ROGAN
*Director of the United States Patent and Trademark Office*